(12) United States Patent
Fuchs et al.

(10) Patent No.: US 6,477,230 B1
(45) Date of Patent: Nov. 5, 2002

(54) X-RAY DIAGNOSTIC INSTALLATION WITH ELECTRONIC ZOOM FOR A DETECTOR WITH A STORAGE LUMINESCENT SCREEN

(75) Inventors: Manfred Fuchs, Nuremberg (DE); Erich Hell, Erlangen (DE); Detlef Mattern, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 62 days.

(21) Appl. No.: 09/675,843

(22) Filed: Sep. 29, 2000

(30) Foreign Application Priority Data

Sep. 29, 1999 (DE) .......................................... 199 46 736

(51) Int. Cl.$^7$ ................................................ H05G 1/64
(52) U.S. Cl. ......................................... 378/98; 250/584
(58) Field of Search ........................ 378/98, 98.8, 98.9; 250/584

(56) References Cited

U.S. PATENT DOCUMENTS 5,049,749 A * 9/1991 Lange et al. ................. 250/584
5,229,608 A * 7/1993 Lange et al. ................. 250/585
5,574,275 A * 11/1996 Durst et al. ............... 250/203.1

* cited by examiner

Primary Examiner—Robert H. Kim
Assistant Examiner—Courtney Thomas
(74) Attorney, Agent, or Firm—Schiff Hardin & Waite

(57) ABSTRACT

An X-ray diagnostic installation has a storage luminescent screen for the latent storage of an X-ray image, an X-ray exposure unit for generating an X-ray beam, a readout system for causing the storage luminescent screen to luminesce by being scanned with a radiation source, a detector for acquiring the light emitted by the storage luminescent screen, and an image playback system. In a first operating mode, the X-ray exposure unit produces X-ray images with a first dose and the readout system implements a fast readout of the image area of the storage luminescent screen with low resolution. In a second operating mode, the X-ray exposure unit produces X-ray images in a limited region with a higher dose compared to the first dose, and this region of the image area of the storage luminescent screen is read out with high resolution.

8 Claims, 3 Drawing Sheets

X-RAY DIAGNOSTIC INSTALLATION WITH ELECTRONIC ZOOM FOR A DETECTOR WITH A STORAGE LUMINESCENT SCREEN

BACKGROUND OF THE INVENTION

1. Field of the Invention

The present invention is directed to an X-ray diagnostic installation of the type having a storage luminescent screen for the latent storage of an X-ray image, an X-ray exposure unit for generating an X-ray beam, and a readout system, which causes the storage luminescent screen to luminesce by being scanned with a radiation source, a detector for the acquisition of the light emitted by the storage luminescent screen, and an image playback system.

2. Description of the Prior Art

German OS 38 03 766 discloses an X-ray diagnostic installation of the above type, wherein a storage luminophore is irradiated with X-rays as a radiation-sensitive transducer, so that unbonded electrons, that are stored in traps, are generated therein. The entire surface of this storage luminescent screen is scanned pixel-by-pixel by an additional radiation source of a readout system, for example a laser, so that the electrons stored in the traps are excited and can fall back into recombination centers, with the energy difference being emitted in the form of light quanta. As a result, it is possible to readout the stored X-ray image from the storage luminescent screen.

For planar scanning of the storage luminescent screen, a laser beam of the type referred to as a "flying spot scanned" is deflected by two mirrors in the vertical and horizontal directions, so that all picture elements lying on the storage luminescent screen are successively scanned. The light emitted by the storage luminescent screen is acquired by two light-guiding plates and is conducted onto two laterally attached, line-shaped CCD light transducers. The output signal of the detector is supplied to a normal video chain for playback of the X-ray image on a monitor.

Europium-activated barium fluoride-bromine chloride compounds disclosed in German OS 33 47 207 that can be excited by visible light (photo-stimulation) can be employed as storage luminophores. A He-Ne laser that generates light at a wavelength of 633 nm is usually for the stimulation of this storage luminophore.

European Application 859 244 discloses an X-ray diagnostic installation wherein the plates of the storage luminescent screens are stimulated region-by-region by a laser with preceding fiber optics instead of by the "flying spot scanner". The emitted light of the irradiated surface is acquired by matrix of CCD image converters which are likewise preceded by fiber optics. For complete scanning of the storage luminescent screen, the readout system is moved over its entire surface.

In such X-ray detectors according to the storage luminophore principle, an X-ray projection image of the patient is first produced and is read out by the scanner and digitized. Such detectors allow only large-format radiographic exposures with a relatively high dose to be made, and these must be slowly read out to obtain full resolution. Subsequent excerpt enlargements with correspondingly adapted resolution (zoom) are not available with such detectors.

SUMMARY OF THE INVENTION

An object of the present invention is to provide an X-ray diagnostic installation of the type initially described that enables a fast synoptic exposure and a subsequent zoom exposure with high resolution.

This object is inventively achieved in an X-ray diagnostic installation operable in a first operating mode wherein the X-ray exposure unit produces X-ray images with a first dose and the readout system implements a fast readout of the image area of the storage luminescent screen with low resolution, and in a second operating mode, wherein the X-ray exposure unit produces X-ray images in a limited region with a higher dose compared to the first dose, and this part of the image area of the storage luminescent screen is read out with high resolution. As a result, a synoptic exposure can be produced first, an image excerpt, and thus a region to be scanned, is then selected, and a high-resolution detail enlargement is then made with electronic zoom.

It has proven advantageous for the scanning (readout) radiation source to be line-shaped and for the detector to be line-shaped and switchable in terms of its resolution.

Inventively, the focusing range of the line-shaped radiation source can be switchable, for example between two focus settings. Given a switchable radiation source, the line width of the CCD is not crucial, so that the line-shaped detector need be switchable between two resolutions only in the line direction.

Optimum adaptations of the installation can be achieved in an embodiment wherein the line-shaped radiation source has two separate arrangements for generating stimulation light at different focus settings and wherein the line-shaped detector has two optically and electrically separate CCD lines with different resolutions.

If a switchable radiation source is not used, then, in the second operating mode, a number of photo-elements can be repeatedly read out simultaneously in the direction of the line width and in chronological succession, their signals being added pixel-by-pixel.

Advantageously, the resolution in the second operating mode can amount to nine times the resolution in the first operating mode, and the dimensions of the active photo-elements for a picture element in the second operating mode can amount to 50$\mu$m and the dimensions of the active photo-elements for a picture element in the first operating mode can amount to 150 $\mu$m.

DESCRIPTION OF THE PREFERRED EMBODIMENTS

Figure 1:
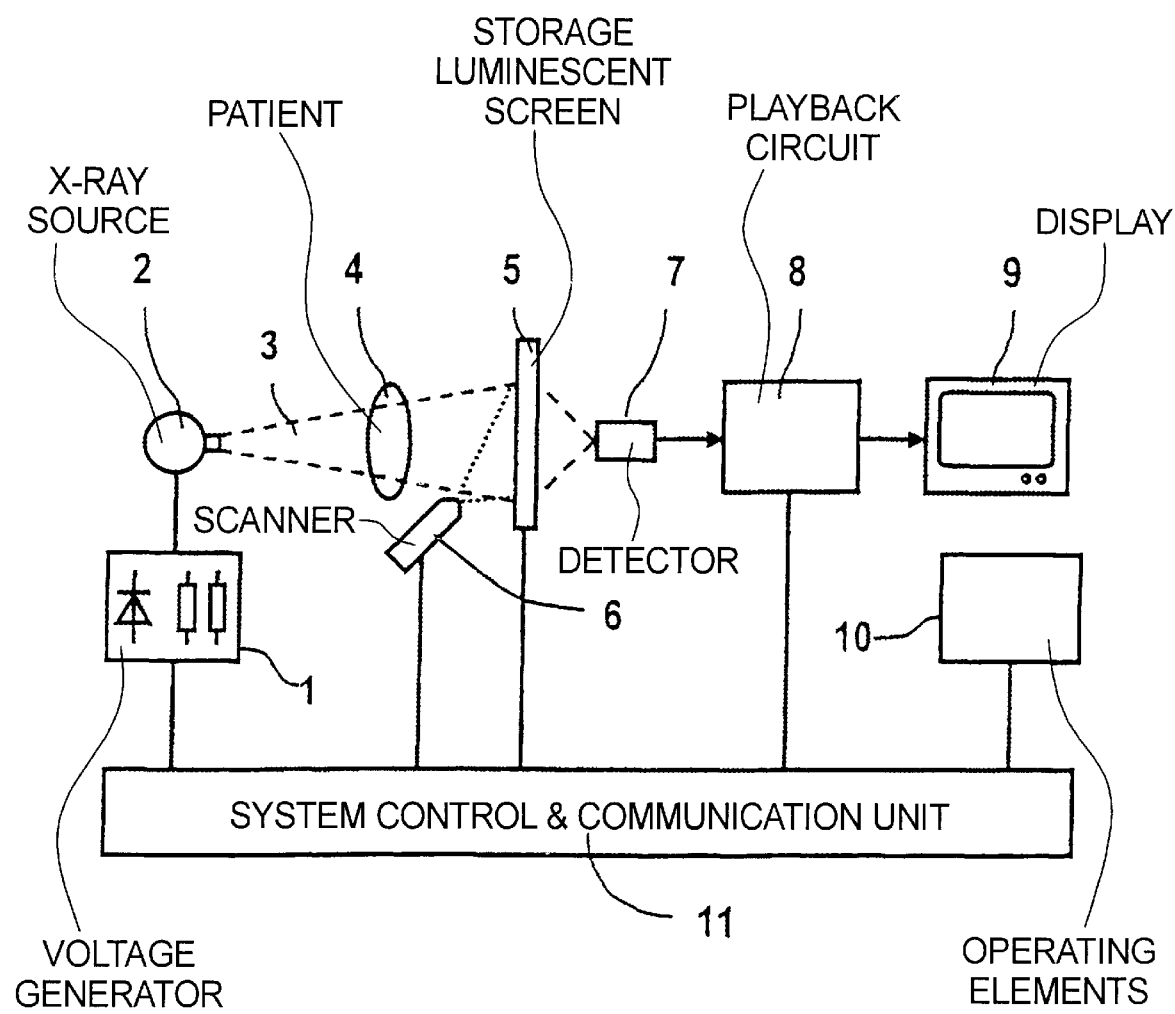
FIG. 1 is a block diagram of a known X-ray diagnostic installation embodying an inventive readout system.

FIG. 1 shows an X-ray diagnostic installation with an X-ray tube 2 supplied with high-voltage and filament voltage by a voltage generator 1. The X-ray tube 2 generates a conical X-ray beam 3 that penetrates a patient 4. The X-rays attenuated by the patient 4 according to the transparency of the patient 4 are incident on a luminescence storage luminescent screen 5. As already described, this incident radiation image generates unbonded electrons in the storage luminescent screen that are stored in traps of the storage luminophore, so that a latent image is stored in the storage luminescent screen 5.

For playback of the latent, stored image, the storage luminescent screen 5 is stimulated line-by-line by a scanner 6. A detector 7 acquires the light emitted by the storage luminescent screen 5 and converts the light corresponding to the brightness of the scanned picture elements into an electrical signal that is supplied to a playback circuit 8 that generates a video signal for display on a monitor 9 from an individual analog output signal of the detector 7. The playback circuit 8 can be an image system with converters, image memories and processing circuits. Operating elements 10 are connected via a system control and communication unit 11 to the other components of the X-ray diagnostic installation. The system control and communication unit 11 effects the control and synchronization of the voltage generator 1, the relative motion of the storage luminescent screen 5 during the scanning, the scanner 6, the playback circuit 8 and the monitor 9.

Figure 2:
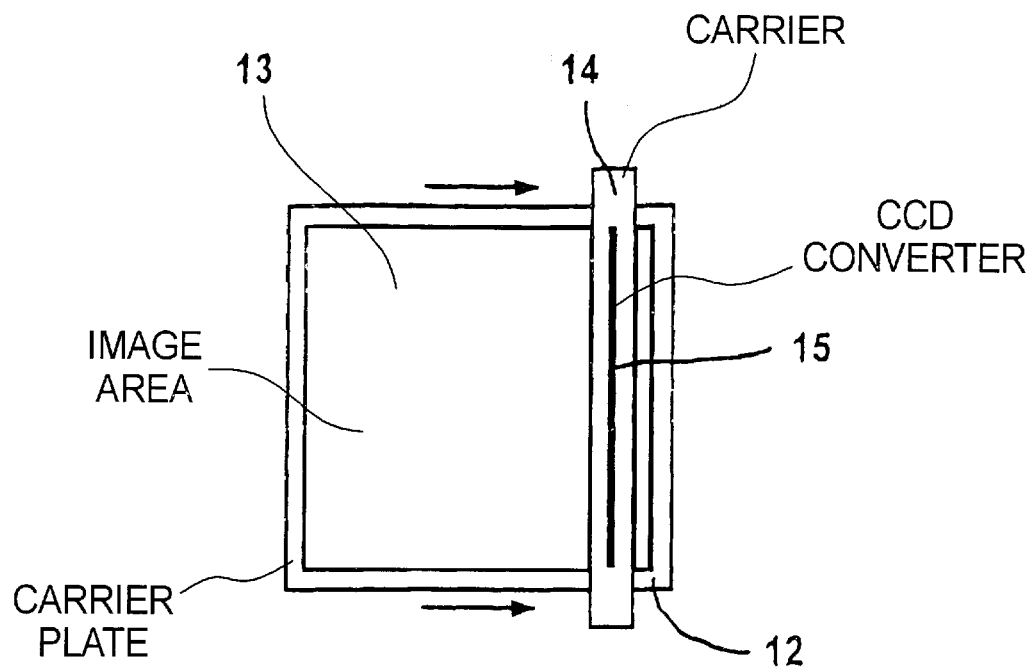
FIG. 2 illustrates an inventive readout system in a first operating mode.

FIG. 2 shows the inventive scanner 6 for the plate-shaped storage luminescent screen 5 in plan view. The screen 5, for example, has a carrier plate 12 of glass with an image region 13. A rectangular carrier 14 straddles the carrier plate 12 of the storage luminescent screen 5. The line-shaped radiation source 6 (not shown) is attached to the carrier plate 12 under the carrier plate 12, and a CCD light converter 15 as the line-shaped detector 7 is attached to the carrier 12 thereabove. As described below, the entire image area 13 can be rapidly scanned with low resolution line-by-line over the entire image width for a synoptic exposure.

Figure 3:
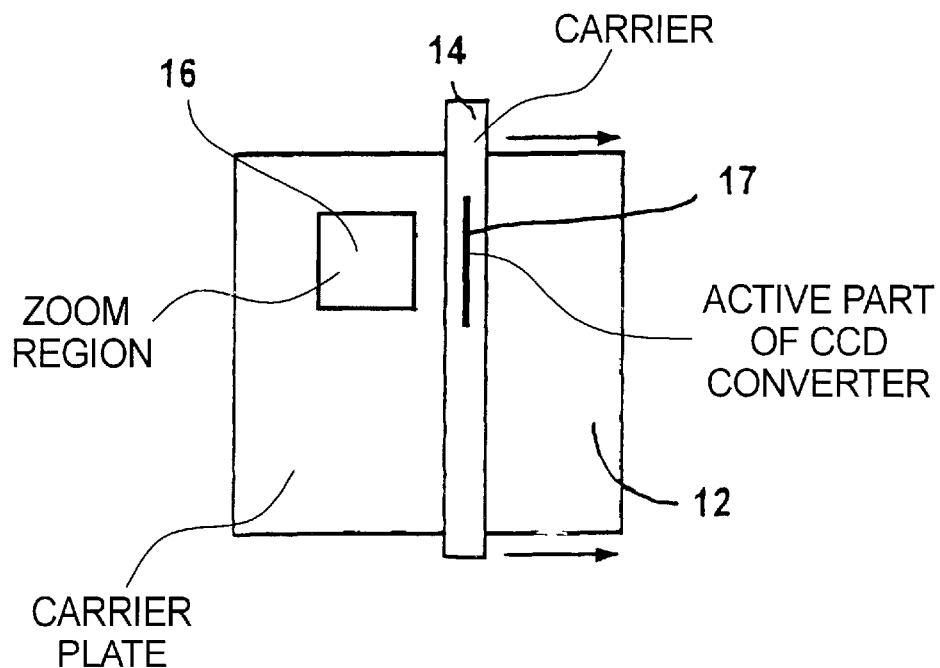
FIG. 3 illustrates the inventive readout system in a second operating mode.

When a particular region of interest (ROI) is selected, then, as shown in FIG. 3, only the zoom region 16 can be read out slowly in a second scan operation and with the highest possible resolution, this region being read out by a small, active part 17 of the CCD light converter 15.

Figure 4:
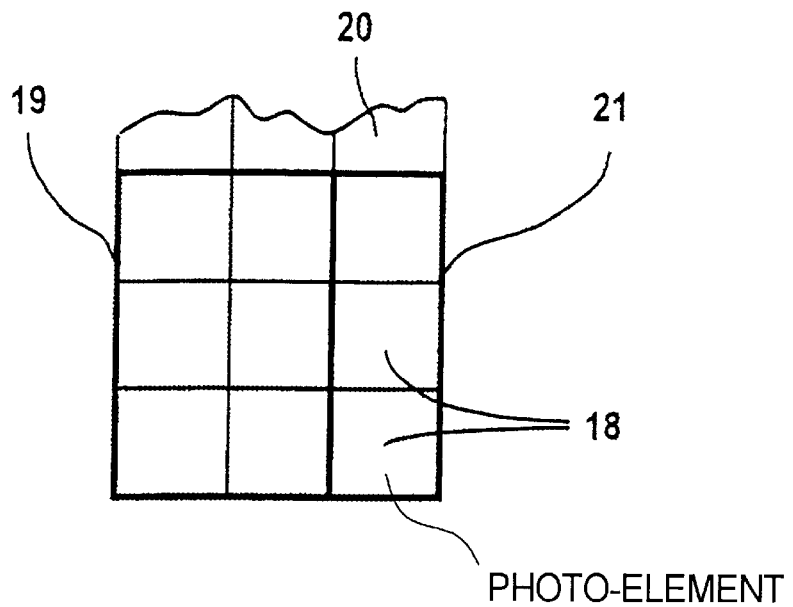
FIGS. 4 and 5 show structural details of the CCD light converter with adaptable resolution in accordance with the invention.

As shown in a fragmented view in FIG. 4, the CCD light converter 15 with adaptable resolution can thereby be composed of a number of photo-elements 18 arranged in three rows. For the first operating mode, the stimulation light of the scanner means 6 is focused such that all photo-elements 18 of the CCD light converter 15 are illuminated by the light emitted by the storage luminophore. By binning, signals from 3×3 photo-elements 18 can be combined into a picture element region 19 and read out in common. For the second operating mode, the photo-elements 18 are read out individually, whereby the readout mode is dependent on the focussing of the stimulation light of the scanner 6.

Given a detector with a storage luminescent screen 5 having such an integrated scanner, exposures are possible at intervals of 5 to 10 seconds. The images also can be viewed at the connected monitor 9 in this time interval.

This allow new, economical possibilities. Large-format synoptic exposures up to 45 cm×45 cm with a reduced dose in quasi-fluoroscopy are possible with the resolution-adaptable and speed-adaptable CCD readout system. After the image has been evaluated by a physician, one or more regions of interest can be registered with high resolution and higher dose for the best image quality without the patient 4 having changed in position. The CCD light converter 15 that directly reads out the storage luminophore plate, for example with a coupled light-guide optics, can, for example, be composed of three lines, and each photo-element 18 can have a size of 50 μm×50 μm.

3×3 pixels are combined (binning) for the synoptic mode. For the same integration time, the speed of the scan head can be 3 times higher than in the high resolution mode. The CCD light converter 15 is electrically connected such that light is integrated over 3×3 photo-elements 18. For the readout, however, all collected electrons of the picture element area 19 are pushed into the lowest line. In this way, only one readout amplifier with the corresponding noise is required. The stimulation light of the scanner 6 is focussed onto a line that is 150 μm wide.

For the high-resolution mode, the 50 μm photo-elements 18 are individually read out. A number of technical embodiments come into consideration for this purpose.

1. The stimulation light of the line-shaped radiation source (scanner 6) remains focussed onto a line that is 150 μm wide.

The CCD light converter 15 is switched to 3 readout lines. One picture element of the storage luminescent screen 5 is now successively read out by the photo-elements 18 of the picture element region 19 in the three lines in succession. The readout of the CCD light converter 15 is accelerated by the factor three. The information of the CCD photo-elements 18 must be correctly allocated to the image pixels and added in the playback circuit 8.

2. The stimulation light is switched to 50 μm focusing.

Now, the line width of the CCD light converter 15 is not decisive. Only the photo-elements 18 are operated on the 50 μm mode in line direction.

3. The stimulation light is likewise switched to 50 μm focusing.

Only the photo-elements 18 in the picture element region 21 of the first line 20 are read out.

Figure 5:
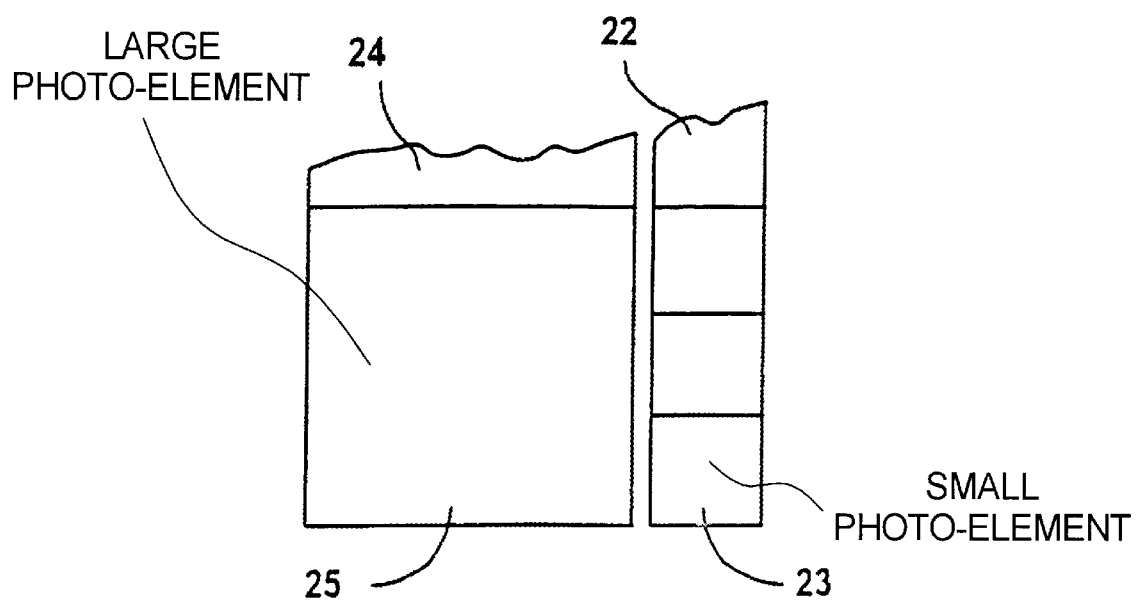

4. The scanner 6 has two lines with arrangements and focussings for the stimulation light optimized for two resolutions. As shown in FIG. 5, the CCD light converter 15 has a first line 22 with small photo-elements 23, for example with a dimension of 50 μm×50 μm, and a second line 24 with, for example, 150 μm×150 μm photo-elements 25 on one chip or on separate chips. The lines 22 and 24 are optically and electrically separated. Depending on the operating mode, the broad or narrow lines of the scanner 6 and of the CCD light converter 15 are selected.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic installation comprising:

an X-ray source which emits an X-ray beam;

a storage luminescent screen for storing a latent X-ray image produced by irradiation of said storage luminescent screen by said X-ray beam;

a readout system for reading out said latent X-ray image from said storage luminescent screen by scanning said storage luminescent screen with a radiation source, and thereby causing said storage luminescent screen to emit light;

a detector for detecting said light emitted by said storage luminescent screen;

an image playback system connected to said detector for converting light detected by said detector into signals for producing a visual, displayable image corresponding to said latent X-ray image; and a control unit, connected at least to said X-ray source and to said readout system, for operating said X-ray source and said readout system in a first mode wherein said X-ray source emits said X-ray beam with a first dose and wherein said readout system executes a rapid readout of said storage luminescent screen with low resolution to obtain a synoptic image, and in a second mode wherein said X-ray source produces said latent X-ray image in a selected limited region of said storage luminescent screen and with a higher dose relative to said first dose, and wherein said readout system executes a readout of said limited region of said storage luminescent screen with high resolution to obtain a zoom image of said selected limited region of said synoptic image.

2. An X-ray diagnostic installation as claimed in claim 1 wherein said radiation source is line-shaped and scans said storage luminescent screen, and wherein said detector is line-shaped and is switchable in resolution at least between said low resolution and said high resolution.

3. An X-ray diagnostic installation as claimed in claim 2 wherein said radiation source has a focusing width, and wherein said focusing width is switchable.

4. An X-ray diagnostic installation as claimed in claim 2 wherein said radiation source has a first focus setting and a second focus setting and is switchable between said first and second focus settings, and wherein said detector has a line direction and is switchable between said low resolution and said high resolution in said line direction corresponding to said radiation source being switched to said first or second focus setting.

5. An X-ray diagnostic installation as claimed in claim 2 wherein said radiation source comprises a first arrangement for generating stimulating light at a first focus setting and a second arrangement, separate from said first arrangement, for generating stimulation light at a second focus setting, and wherein said detector comprises a first CCD line having a first resolution for use with said first focus setting and a second CCD line having a second resolution for use with said second focus setting, said first and second CCD lines being optically and electrically separated from each other.

6. An X-ray diagnostic installation as claimed in claim 2 wherein said storage luminescent screen is comprised of a plurality of photo-elements, said plurality of photo-elements comprising groups of photo-elements with each group of photo-elements representing a pixel, and wherein said control unit, in said second operating mode, operates said readout system to simultaneously readout a plurality of said photo-elements simultaneously in a line width direction, and multiply in chronological succession, to obtain a plurality of signals respectively representing said pixels, and wherein said detector system adds said signals pixel-by-pixel.

7. An X-ray diagnostic installation as claimed in claim 1 wherein said control unit operates said readout system in said second operating mode with said high resolution being nine times said low resolution in said first operating mode.

8. An X-ray diagnostic installation as claimed in claim 1 wherein said storage luminescent screen in comprised of a plurality of photo-elements, said plurality of photo-elements comprising a plurality of groups of photo-elements respectively comprising pixels and wherein each photo-element has a dimension, and wherein said photo-elements which are active for comprising pixels in said second operating mode have a dimension of 50 $\mu$m and wherein photo-elements which are active for forming pixels in said first operating mode have a dimension of 150 $\mu$m.

* * * * *